United States Patent
Gaskell

(10) Patent No.: US 8,544,472 B2
(45) Date of Patent: Oct. 1, 2013

(54) DENTAL DEVICE

(75) Inventor: John Gaskell, Dandenong (AU)

(73) Assignee: MDSA Pty Ltd, Victoria (AU)

( * ) Notice: Subject to any disclaimer, the term of this patent is extended or adjusted under 35 U.S.C. 154(b) by 1388 days.

(21) Appl. No.: 11/070,621

(22) Filed: Mar. 2, 2005

(65) Prior Publication Data

US 2006/0196512 A1    Sep. 7, 2006

(51) Int. Cl.
*A61F 5/56*     (2006.01)
*A61C 7/08*     (2006.01)

(52) U.S. Cl.
USPC ........... 128/848; 128/859; 128/861; 128/862; 128/202.27; 433/36; 433/37; 433/38; 433/41; 433/48; 602/902

(58) Field of Classification Search
USPC ....... 128/206.29, 201.26, 846, 848, 853–863; 602/902; 2/2; 433/36–38, 41, 43, 48; D24/180
See application file for complete search history.

(56) References Cited

U.S. PATENT DOCUMENTS

| 5,427,117 | A | | 6/1995 | Thornton | |
|---|---|---|---|---|---|
| 5,566,683 | A | * | 10/1996 | Thornton | 128/848 |
| 5,829,441 | A | * | 11/1998 | Kidd et al. | 128/848 |
| 6,055,986 | A | | 5/2000 | Meade | |
| 6,305,376 | B1 | * | 10/2001 | Thornton | 128/848 |
| D450,850 | S | * | 11/2001 | Gaskell | D24/180 |
| 6,729,335 | B1 | * | 5/2004 | Halstrom | 128/848 |
| 6,845,774 | B2 | * | 1/2005 | Gaskell | 128/848 |
| 7,159,591 | B2 | * | 1/2007 | Kussick | 128/848 |
| 2002/0000230 | A1 | * | 1/2002 | Gaskell | 128/848 |
| 2003/0217753 | A1 | * | 11/2003 | Thornton | 128/848 |
| 2005/0028827 | A1 | * | 2/2005 | Halstrom | 128/861 |
| 2006/0174897 | A1 | * | 8/2006 | Sarkisian | 128/859 |

FOREIGN PATENT DOCUMENTS

| WO | WO 95/08969 | 4/1995 |
|---|---|---|
| WO | WO 95/33418 | 12/1995 |
| WO | WO 98/46177 | 10/1998 |
| WO | WO 00/15283 | 3/2000 |

* cited by examiner

*Primary Examiner* — Clinton T Ostrup
(74) *Attorney, Agent, or Firm* — Dinsmore & Shohl LLP

(57) ABSTRACT

A fastener suitable for connecting two parts of a dental splint together in a prearranged or predetermined spatial relationship to treat a person suffering from a sleep disorder is described. In one form the fastener comprises a base member and a cover member arranged to define a cavity therebetween. A movable connector is located within the cavity, the movable connector interconnecting the two parts of the dental splint. The fastener has an adjustor movably connected to the connector such that the position of the connector is moved in response to movement of the adjustor by adjusting the position of the adjustor, the connector in the form of a hook moves the other part of the dental splint so as to reposition the jaws of a person being treated for the sleep disorder.

28 Claims, 3 Drawing Sheets

DENTAL DEVICE

The present invention relates generally to dental devices. More particularly, the present invention relates to dental devices for insertion into the mouth of a person suffering from one or more forms of a sleep disorder so as to prevent the incidence of snoring and/or to provide improved breathing during sleep thereby treating the sleep disorder and/or to ameliorate the adverse effects of snoring and other sleep disorders. Even more particularly, the present invention relates to dental splints, such as for example mandibular splints or the like, and in particular to an improved adjustable fastener of the type suitable for use with dental splints, such as for example, to adjustably connect together the upper and lower arches forming the splint. Even more particularly, the present invention relates to a fastener for connecting the two parts of a two piece dental splint together so as to maintain the two parts in relationship to one another in such a manner that at least a part of the two pieces is maintained at a predetermined spatial relationship with respect to the other pieces when inserted into the mouth of a patient suffering from the sleep disorder whilst the patient is asleep. Furthermore, the fastener is provided with an adjustor for use in adjusting the position of one part of the splint with respect to another part of the splint to provide treatment of the sleep disorder. The purpose of the adjustable splint is to adjust and maintain the upper jaw and lower jaw with respect to each other to promote opening of the air breathing passageway to alleviate snoring and its adverse effects. In particular, the position of the lower jaw is adjusted forwardly of the position of the upper jaw by movement of the fastener.

Although the present invention will be described with particular reference to one form of the fastener and one form of the dental device having the fastener it is to be noted that the scope of the present invention is not limited to the described embodiments but rather the scope of the present invention is more extensive so as to include other arrangements and forms of the dental device and/or the fastener and/or of the two pieces or arches forming the splint and the use of the various forms of the device in other applications.

Many people suffer from snoring and its effects. Whilst about 8% of the population, in Australia, suffer from some form of seriously debilitating sleep disorder up to about 20% of the population have a snoring problem of some sort that adversely affects their health to a lesser or greater extent. Similar numbers of people in other countries also suffer from some sort form of sleep disorder including sleep apnoea. The adverse effects of snoring not only affect the snorer but also affect those within earshot of the snorer. Previous attempts to provide devices for preventing snoring or improving breathing during sleep have not been entirely satisfactory for a variety of reasons.

One problem associated with existing anti-snoring devices, such as dental splints, is that they are not adjustable and are of the "one size fits all" type which are not adaptable to the specific requirements of the individual having to use the device. In this type of dental splint which comprises an upper arch connected to a lower arch by a suitable connector, the relative positions of the upper and lower arches with respect to each other cannot be adjusted since the connector is not adjustable. The connector by which the lower jaw is extended forward by forward movement of the lower arch is not adjustable by the user thereby resulting in possible discomfort whilst using the splint as well as the splint being ineffective in treating the sleep disorder.

Another type of dental splint is of the fully customised variety which requires fitting by a skilled person such as a dentist or an advanced dental technician or similar and/or requires custom manufacture of the device in a factory or laboratory both of which add considerably to the cost of the device since such splints are one off devices. In the past the cost of having a fully customised dental device fitted by a dentist or equivalent health worker could be in excess of many hundreds of or even thousands of dollars. Also, during treatment often it was not possible to change the shape or orientation of the splint since it was not adjustable. Any adjustment that was necessary required manufacture of a new splint which added to the cost.

In dental devices previously available, when provided with adjustment, the adjustment was either difficult to use, unsafe to use, the splint itself was excessively large or the components small enough to be swallowed, placed undue strain on one or other of the upper or lower jaw, or for a variety of other reasons was not satisfactory. In some instances the components forming the splint including the adjustor or similar mechanism, separated from the splint and owing to their small size were swallowed or caused other health problems particularly if the small sized components were insecurely attached to the splint or worked themselves loose during use. Thus, such splints were difficult to use, uncomfortable to wear, were not effective or were injurious to use.

Therefore, there is a need to provide a dental splint that can be used to reduce or eliminate snoring and provide improved breathing during sleep that is easily and readily adjustable by the person wearing the splint and can be readily fitted to the exact requirements of an individual at a inexpensive or reasonable cost i.e. has all the attributes of a custom made dental splint but without the high cost, is easier to adjust in use and is more comfortable to wear, particularly for extended periods at night, is more securely assembled, and the like thereby providing a wider range of individuals with the opportunity of treatment for sleep disorders at lower cost.

Thus, it is an aim of the present invention to provide a fastener suitable for use in adjustably connecting together the two arches of a dental splint or dental appliance that will reduce or eliminate snoring and/or provide improved breathing during sleep, that is comfortable to use, offers greater adjustment, is more effective and is available at a lower cost.

One problem of existing fasteners similar to the fastener of the present invention is that such fasteners have too large a profile or size to accommodate use by all members of the population. In some instances the fastener and/or the splint is too large and bulky. When such fasteners were formed into a splint, the splint had too large a profile or size which prevented the lips of a person closing together during sleep. One reason for this is that the fastener was too large or bulky. One contributing reason for being too large or bulky is that the fastener needed to have a flange at the front of the fastener. The flange was thought necessary to assist in both locating the fastener correctly with respect to the arch to which it was fitted and to correctly locate the arch centrally within the mouth. If the flange was not present, the fastener could not be readily centrally located with a movable tray on either side and the arch could not be readily located on the correct teeth within the mouth since the flange provided a reference or datum point for the two arches forming the splint. However, there was a tendency for the flange to be exposed during use, particularly during prolonged use of the splint which had the risk that the front teeth of a person located within the arch member near the flange could contact the inside surface of the flange causing discomfort. Whilst this problem did not detract from the performance of the arch or splint and did not cause injury or other health problems, it was uncomfortable and annoying. Another problem that became manifest during use was that the flange had a tendency to cut or lacerate the inside of the mouth or the lips during use as it became exposed. The tendency of the flange to lacerate was exacerbated by the grinding movement of the teeth caused by bruxism as a person slept. The repeated sideways movement back and forth caused laceration of the mouth and lips. Thus, the appeal and acceptance of the fastener could be the improved if the flange was removed since not only could the fastener adopt a lower profile but it lessened the chance of laceration of the mouth and lips.

However, owing to the manner in which the arch member was formed using a relatively soft and runny polymeric liquid within the tray for forming the arch into the exact shape of the teech, the flange was also needed to retain the polymeric material inside the tray of the arch from escaping over the front side of the fastener. In effect, the flange acted as a wall or barrier to the flow of the polymeric material from the tray when it was in an uncured condition which would have resulted in there being insufficient soft polymeric remaining in the tray to mould the material and arch to the exact shape of the teeth. The flange formed a continuation of the side walls of the tray forming the wings movably connected to the fastener.

Surprising, it has been discovered by the inventor that, in order for the fastener and the splint to be able to adopt a lower profile, the flange can now be omitted from the fastener owing to the different method being used to form the arch member and splint since the use of a hard tray to retain the soft polymeric material is no longer required. Rather, a single double laminate functional polymeric material only is used to form the splint and the fastener is embedded or adhered to this material to form the arch member.

Another problem associated with existing fasteners is that during use when subjected to grinding caused by bruxism, the various components of the fastener had a tendency to work loose, which in extreme cases could lead to components separating from the main body of the fastener. This tendency was caused, in part, by the method of construction in which parts of the fastener were bent, folded or punched over another part, such as the prongs of the cover being folded over the base plate or similar. Thus, there is a need to more securely attach the various components together to reduce or eliminate the chance of the components separating.

Another problem of existing fasteners and/or splints is that dental technicians and other health workers fitting or installing the splint had to guess initially at the position that the connector in the form of a hook was to adopt for the splint to be operational. It was only when the splint was inserted into the mouth could the final position of the hook be adjusted. Often, the guess at the position of the connector was incorrect, sometimes widely incorrect so that, significant adjustment was necessary before the final position could be reached. This excessive adjustment of the splint within the mouth of the person was aggravating and uncomfortable. Thus, there is a need to be able to more accurately adjust the position of the connector prior to inserting the splint into the mouth. In one embodiment, this problem is addressed by having a scale to provide information about the position of the connector.

Therefore, it is an aim of the present invention to provide a fastener which at least partially addresses at least one of the shortcomings of prior art fasteners as described in this specification. It is to be noted that not all embodiments of the fastener address all of the problems. Different embodiments address different problems. Some embodiments can address two or more problems.

In the past, some forms of dental splints have been only available as complete units including the upper arch, the lower arch and a fastener for coupling the two arches together including both adjustable fasteners and fixed fasteners. Such customised units or one size fits all units were expensive and required the services of trained personnel over a number of different steps in the diagnosis, manufacture, fitting and use of the devices. One of the contributing costs was that the fastener and arches were only available as complete integral units. As upper and lower arches are generally commonly available devices and are routinely used for a variety of purposes, they are readily available to skilled and non skilled personnel usually at a low cost. If a new form of fastener was made available the existing upper and lower arches could be utilised with the fastener to produce low cost dental splints. Surprisingly, the inventor of the present invention, has been able to provide a more universal type fastener that is capable of being attached to either the upper or lower arch thereby resulting in an effective low cost dental splint. Therefore, one of the aims of the present invention is to provide a fastener which can be supplied to dentists, dental technicians or other health workers as a single unit separate from the arches or other parts of the splint for attaching to and for use with upper and lower arches without the need to provide complete dental devices.

According to one aspect of the present invention there is provided a fastener having a lower profile suitable for connecting two parts of a dental splint together in a prearranged or predetermined spatial relationship in use when treating a person suffering from a sleep disorder, said fastener comprising a base member and a cover member located with respect to each other so as to form a cavity or chamber intermediate the base member and cover member, wherein at least a part of a movable connector is located within the chamber or cavity and wherein there is an adjustor movably connected to the connector such that the position of the connector is moved in response to movement of the adjustor to adjust the dental splint, said connector interconnecting the two parts of the dental splint so as to move one part of the splint with respect to the other part of the splint in response to movement of the adjustor so as to adjust the splint.

Typically all of the components of the fastener are made from metal, preferably, steel and more preferably stainless steel and most preferably of a grade of stainless steel suitable for internal use within a human body. Even more typically, the components are hand worked and vibration polished to remove all sharp edges, burrs or similar.

Typically the base member of the fastener is a base plate. More typically, the base plate is generally planar. More typically, the base plate is provided with a main body portion and two side portions. Typically, the body portion is centrally located. More typically, the body portion is located intermediate the side portions which are located on either side of the body portion.

Typically the fastener is provided with a locator for assisting in accurately locating the fastener when forming and/or installing the splint. More typically, the locator is the adjustor. Typically, the adjustor is located centrally within the fastener and is located at or towards, or is accessible from the front of the arch member of the splint in use. More typically, the position of the adjustor acts as the locator for centrally locating the fastener on the arch member to which it is attached. More typically, the adjustor is located centrally within the fastener. Even more typically, the fastener is located substantially centrally within the arch member to which it is attached.

Typically the connector is a hook, clip, clasp, post, projection or similar, preferably having a bent, folded, curved, looped, arcuate or other similar shaped portion. More typically, the hook, etc is movable with respect to the base plate and/or cover. Even more typically the hook is provided with a shank and a curved portion or tip portion. More typically, the shank of the hook is provided with an internally threaded aperture or bore for receiving an externally threaded shaft or similar so that rotation of the shaft within the aperture or bore moves the hook with respect to the base plate and/or cover. More typically the hook is part of a set-screw of similar adjustment mechanism. More typically, the adjustor is the threaded shaft, set-screw, thrust screw or the like. More typically, the adjustor is held captive with respect to the fastener, typically, held captive within the cavity formed between the base plate and cover.

Typically, the adjustor is a bolt having a head and an externally threaded shank. More typically, the head is provided with a flange, skirt, collar or other enlarged portion. More typically, the enlarged portion is held captive within the cavity and prevents the bolt from being displaced or dislodged from within the cavity yet allows the bolt to rotate to move the connector.

Typically, part of the cover is spaced apart from the base plate when the base plate and cover are assembled together, so as to form the cavity, cage, enclosed space or similar. More typically, the hook is located intermediate the base plate and the cover. Even more typically, the cover is provided with a slot through which a part of the hook, preferably the shank is received. More typically, the shank of the hook moves in the lengthwise extending direction of the slot in response to movement of the adjustor. More typically, the cover is provided with side walls. Even more typically, the side walls are provided with apertures, cut outs, or the like allowing access to the head of the adjustor. More typically, the size of at least one of the apertures is less than the size of the enlarged collar of the adjustor.

Typically the fastener includes at least one attachment element, preferably two attachment elements. More typically, the attachment element(s) is a flap, tab, tag or similar extending outwardly from the base plate, preferably the attachment element is a side portion on either side of the base plate. More typically, the attachment element is the side portion of the base plate. More typically the tab, etc. is provided with an aperture or a projection to assist in attaching the fastener to the arch. Even more typically there are two attachment elements extending in opposite directions from opposed sides of the base plate, typically the central main body. More typically, the tabs, etc. are angularly inclined to the base plate. Even more typically, the tabs, etc. are in stepped relationship with the base plate. Even more typically, the tabs are generally planar, preferably arranged substantially coplanar within the plane of the base plate so that the base plate can adopt a low profile allowing a person wearing the splint to close their lips whilst wearing the splint. Alternatively, the tabs are in stepped and angularly inclined relationship to the main body portion.

Typically the or each arch member is a one piece member. More typically, the arch member is a substantially arcuate shaped member, and even more typically an arcuate member that is molded or cast to the exact profile of the teeth to which the arch is fitted. Typically, the arch is a single material or single layer of material or is made from two or more layers of material. More typically, the arch is made from a relatively soft and a relatively hard layer. More typically, the arch is made from a thermoplastic material, preferably, a polymeric material. Preferably, the material is a double laminate functional dental splinting material having an inner portion which is relatively softer than the outer portion which is relatively harder. Preferably, the arch is made from ERKLLOC PRO.

Typically the fastener is connected to one of the arch members forming the splint. More typically the arch member is an upper arch member, although in some embodiments the arch member can be the lower arch member. More typically, the fastener is attached to the arch member by the attachment element or elements. Even more typically, the arch and fastener are connected or bound to each other by an adhesive. Typically, the adhesive is located through the aperture or around the projection of the attachment element. Typically, the adhesive is a thermoplastic material, preferably a polymeric material and more preferably an acrylic polymeric material. Even more typically, an impression of the teeth of the person using the splint is produced by holding the material when in a softer state against the teeth for a sufficient period of time to form the impression.

Typically, the fastener is a low profile fastener not having an upstanding flange, the base plate being essentially planar and the cover being welded to the base plate so as to obviate the need for prongs of the cover being bent over the base plate. Instead, the cover and base plate are welded or otherwise adhered together without any protruding fitting.

Typically, one of the arches is provided with an engagement element for engaging with the connector. More typically, the engagement element is in a complementary form of the connector. Even more typically, the engagement element includes a lip, shelf, groove, slot, flange, plate or similar. In one embodiment, the engagement element is a planar form of the base plate without the locator or flange. Typically, the engagement element is the edge of the planar plate. More typically, the lip, etc faces rearwardly or is rearwardly directed and is located at or towards the centre of the arch member. Even more typically, the hook, etc. is provided on the other arch member and the lip, etc. is provided on another arch member. More typically, the tip, etc. of the hook of the connector on one arch member engages with the lip, etc. on the other arch member so that movement of the hook causes corresponding movement of the arch member having the lip, etc. to bring forward the jaw to which the arch member having the lip with respect to the other jaw thereby altering the shape of the airway to reduce or prevent snoring and/or to treat the sleep disorder. Typically, adjustment of the connector forces the lower jaw forward by engagement with the engagement element.

Typically, the fastener is manually adjustable using a special tool such as an allen key or hexagonal shaft or the adjustor is motorised such as, for example, by using a diode motor or microvolt motor to automatically extend the lower jaw forward by adjusting the position of one arch member with respect to another arch member. More typically, the adjustment is continuously variable or is step wise variable.

The present invention will now be described by way of example with reference to the accompanying drawings in which:

FIG. 3b is a top perspective view of the outer surface of the fastener of FIG. 3a;

Figure 1:
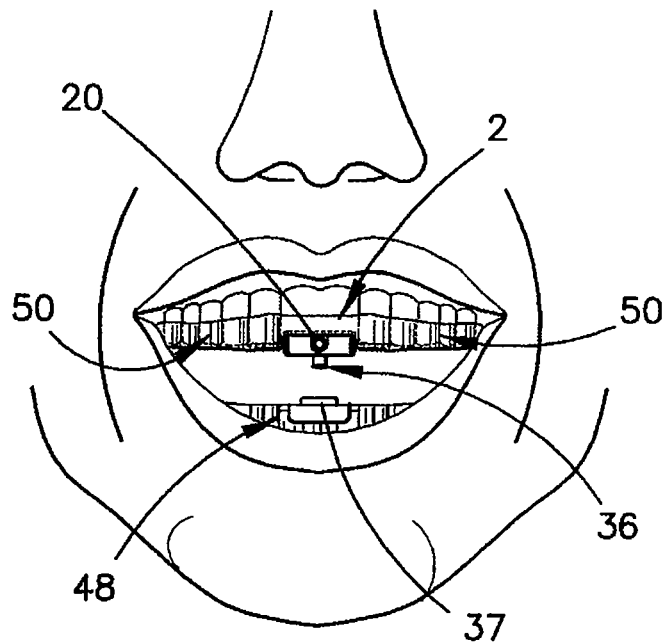
FIG. 1 is a front view of one form of a dental splint located in situ within the mouth of a person using the splint in which the fastener of the present invention is attached to the upper arch of the splint and the upper and lower arches are not connected together by the connector of the fastener thus allowing the person to open their mouth.

With particular reference to FIGS. 2, 3a, 3b and 4, one form of the fastener of the present invention will be described. The fastener which is generally denoted by reference number 2 is in the form of a generally double tab set screw that comprises four individual components as is shown more particularly in exploded form in FIG. 4. The components are base plate 4, cover 20, hook 36 and threaded allen headed bolt 44.

Figure 4:
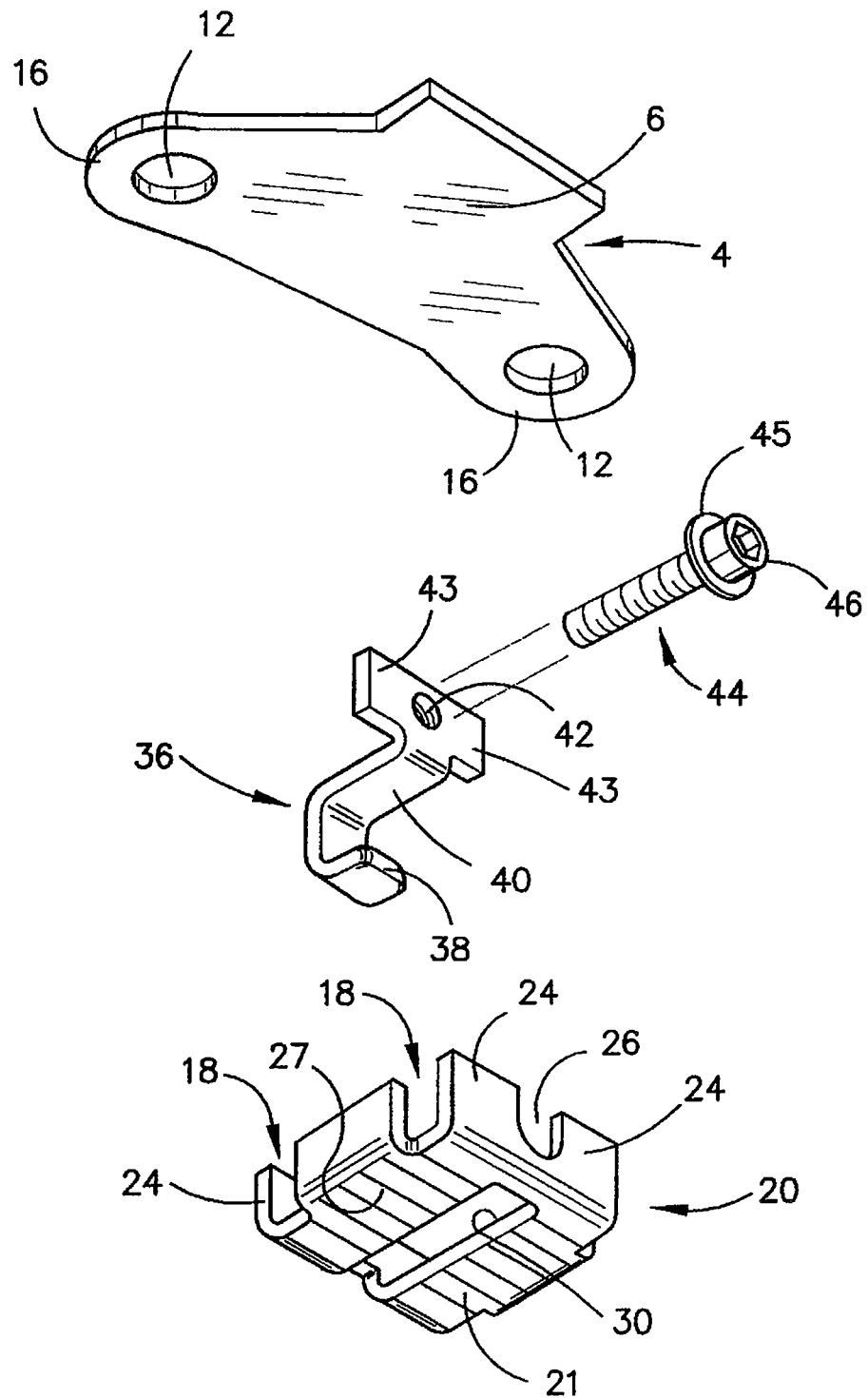
FIG. 4 is an exploded isometric view of the fastener of FIGS. 3a and 3b showing the components of the fastener separated from one another.

With particular reference to FIG. 4, the first of the components is a stainless steel base plate, generally denoted as 4, which has been hand worked and vibration polished to remove all sharp edges, burrs or the like and to produce radiused edges and corners. Base plate 4 includes a centrally located generally square or rectilinear planar main body portion 6 which is provided with a pair of opposed square cut-outs or apertures at or towards opposite side edges of body portion 6.

In some embodiments the fastener has a locator whereas in other embodiments the locator is absent from the fastener. In one form, the locator is the adjustor. Thus, alien bolt 44 can also be used as a locator. The position of allen bolt 44 is used to centrally locate the fastener on the arch and in the mouth in the correct position. It is to be noted that the head of alien bolt 44 is located at or towards the front of the arch member to which it is attached.

A pair of substantially planar opposed tabs 16 extend outwardly from opposed sides of body portion 6. It is to be noted that the pair of tabs 16 extend from the sides of body portion 6. In some embodiments, each of the tabs 16 is provided with a shoulder along the edge adjacent to the side edge of body portion 6 to displace the level of tabs 16 from being in the plane of body portion 6 into being in a stepped relationship with the body 6. In other embodiments, as illustrated tab 16 may extend in the same plane as body portion 6. In still other embodiments, tabs 16 may be inclined to the body portion 6 so as to be angularly inclined to body portion 6 rather than being in a stepped relationship. In other embodiments, tabs 16 may be both in stepped relationship and be angularly inclined with main body 6. Irrespective of the relationship to main body 6, each tab 16 is provided with a circular aperture 12 to assist in connecting the fastener to the arch. Tabs 16 form part of the attachment element for attaching the fastener to the respective arches to form either the upper arch or lower arch. Alternative forms of the attachment elements are possible. It is to be noted that a particularly preferred from of the base plate 4 is where tabs 16 are coplanar with body 6 so that the fastener can adopt a low profile within the splint to allow a person using the splint to fully close their lips during use of the splint so that use of the splint is more comfortable.

Figure 2:
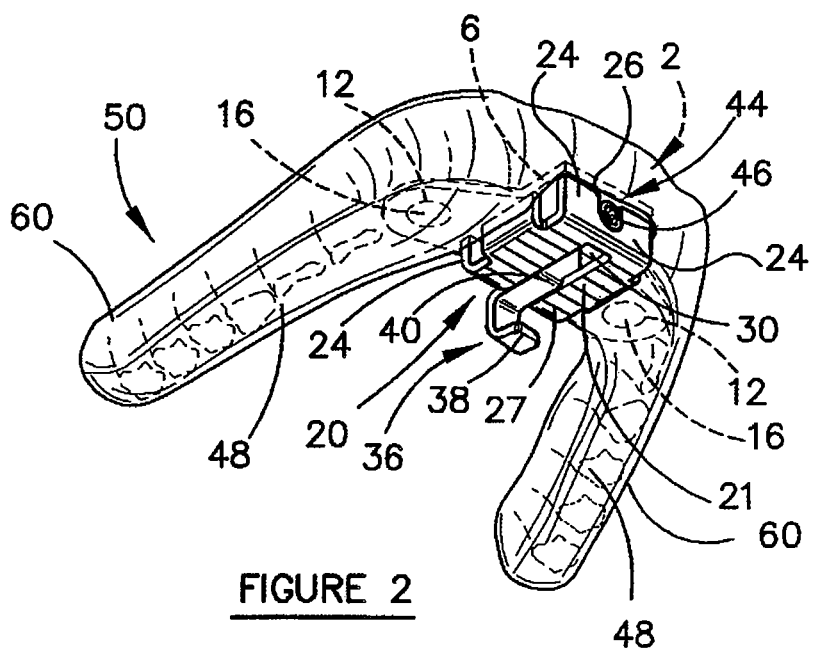
FIG. 2 is a view of one form of the fastener of the present invention connected to one of the arches forming the dental splint of FIG. 1.
Figure 3A:
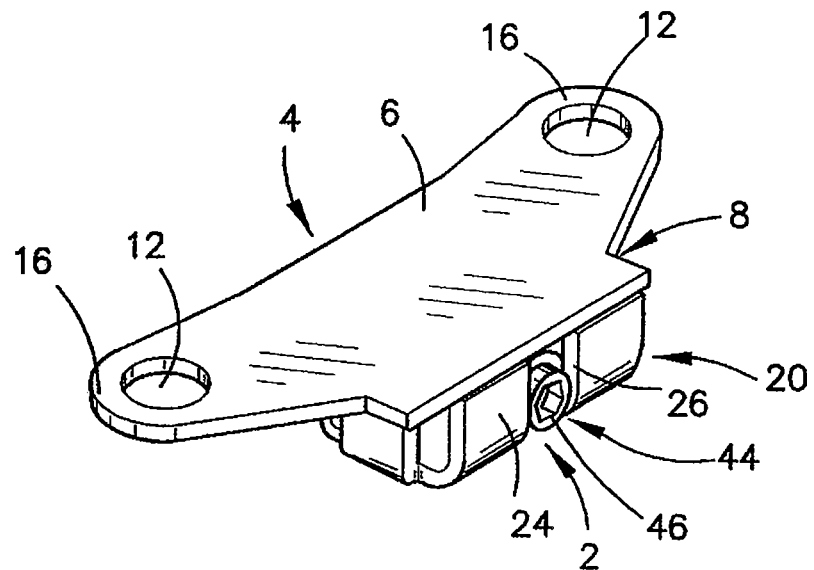
FIG. 3a is a top perspective view of the inner surface of one form of the fastener of the present invention.
Figure 3B:
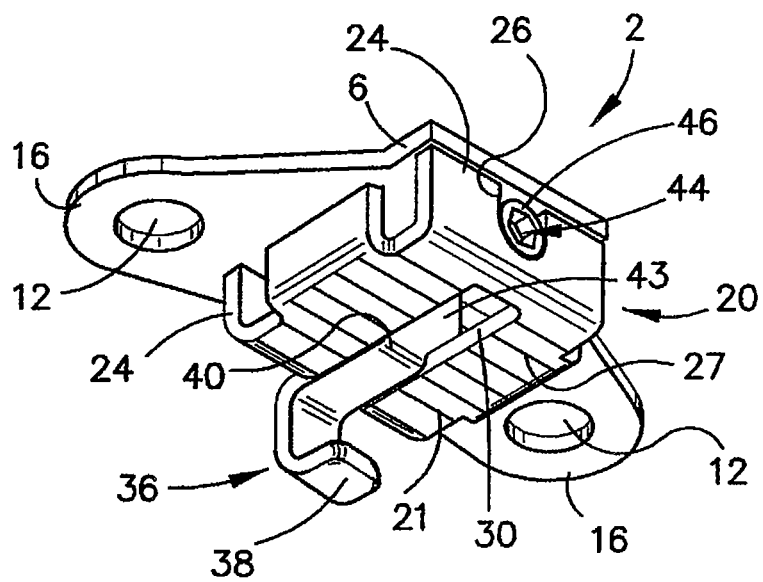

A stainless steel cover 20 which has also been hand worked and vibration polished to remove all sharp edges, burrs or the like and the edges and corners radiused is located in intimate contact with base plate 4 as shown more particularly in FIGS. 2, 3a and 3b. Cover 20 is in the form of an open side box arrangement having an outer face portion 21 and four side portions depending from the face portion 21 in a direction towards base plate 4. Each corner of cover 20 is open so that the sides are spaced apart from each other. In one embodiment, one pair of sides is provided with a pair of outwardly depending projections in the form of prongs, tangs, tabs, fingers or similar projections. In use in forming fastener 2 prongs are received in respective square apertures and are bent, folded, twisted, deformed or the like so as to securely retain cover 20 in place on base 4 with a cavity, chamber, space or the like being formed between the base plate 4 and cover 20. In other embodiments, the ends of the prongs are removed flush with the outer surface of base plate 4 so that they do not project outwardly from base plate 4. The end of prong within a suitable aperture is welded or otherwise adhered to base plate 4 by any suitable means, such as welding. Welding results in the base plate and cover being more securely connected to each other to prevent the components becoming or working loose during use of the splint. Base plate 4 effectively closes the open surface of cover 20. It is to be noted that in some forms of the fastener of the present invention, the ends of the prongs do not extend beyond base plate 4 or the plane of body 6, particularly the inboard surface of base plate 4 when formed into an arch as described. Rather the end of the prongs are substantially flush with the surface of base plate 4 to assist the fastener being located within the arch member and reducing the size or bulk of the fastener so that the splint can adopt a low profile within the mouth.

One of the side walls 24 of cover 20 is also provided with a cut-out, aperture, opening 26 or the like centrally located therein. The depending parts of side walls 24 are located at regularly spaced apart locations around the periphery of the cover 20 in order to space face 21 from body portion 6 of base plate 4 so as to define the cavity, chamber or similar therebetween. Aperture 26 located along one of the side walls 24 allows access into the cavity defined between the cover and base plate. Aperture 26 is located on the front side of fastener, so as to allow access to the adjustor located within the cavity as will be described in more detail later in this specification. Face portion 21 is provided with slot 30. In use, aperture 26 is accessible through the mouth of the person wearing the dental splint as shown in FIG. 1 to allow the splint to be adjusted in situ during use by moving the adjustor with a suitable tool.

In one embodiment, front face 21 is provided with an indicator in the form of a measure, scale, graduations or the like, to provide an indication of the extent of movement of hook 36. In one form the graduations are a multitude of lines, marks, scoring or the like 27 located in regularly spaced apart relationship to each other to provide a scale for measuring the position that hook 36 should adopt to provide the correct adjustment of the splint within the mouth to treat the sleep disorder.

A connector in the form of a hook 36 is provided within the cavity of fastener 2. Part of hook 36 is located within the cavity formed intermediate cover 20 and base plate 4 with the distal end or tip 38 of the hook 36 extending beyond cover 20 and shank 40 of hook 36 being received through slot 30. Tip 38 takes the form of a generally bent or folded configuration. The part of shank 40 located with the cavity is provided with an internally threaded aperture 42 for receiving a threaded allen bolt 44, stud or similar device. The end of hook 36 having the threaded aperture 42 is also provided with a pair of oppositely directed arms 43 in a generally T-shape so as to extend outwardly of the hook to assist in retaining hook 36 within the cavity.

The head 46 of threaded allen bolt 44 is provided with an enlarged collar 45 or the like to prevent bolt 44 from being dislodged or displaced from the fastener by holding bolt 44 captive within the cavity.

Hook 36 is free to move along the lengthwise extending direction of slot 30 in response to rotation of allen bolt 44. Hook 36 is one form of the connector of the fastener of the present invention. It is to be noted that other forms of the connector are possible. Movement of the position of the hook 36 in slot 30 with respect to cover 20 and base plate 4 provides for adjustment of the two arches forming the dental splint as will be described in more detail later in this specification.

With particular reference to FIGS. 1 and 2, one form of the arch member of the present invention will be described. This form of the arch member is the upper arch member. It is to be noted that two arch members being a lower arch 48 and an upper arch 50 form the dental splint, such as the mandibular splint of the present invention as shown in FIG. 1. The two arch members are interconnected together by hook 36 engaging lip 37 in the other arch member whereby one of the arch members which is typically the upper arch member 50 has the fastener 2 of the present invention attached thereto and the other arch member, typically the lower arch member 48, has a complementary connecting means 37 such as for example the lip edge, flange, loop, plate or the like for receiving the hook. The hook 36 is received in the lip to maintain the two arch members 48,50 in their spatial relationship to each other during use of the splint when the two arches 48,50 are connected together.

One embodiment of the mandibular splint having the fastener of the present invention will now be described. Upper arch member 50 includes two side wings 60, one on either side of fastener 2 positioned centrally within the arch member. Lower arch member 48 includes lip 37 and two side wings 60.

The complementary connecting means or receiving means 37 fitted to the arch member not having fastener 2 can take any number of suitable forms. One form is a lip, shelf, ledge, plate, flange or similar formed centrally in the arch member and facing rearwardly into the mouth cavity. The tip 38 of hook 36 which is forwardly directed or forwardly facing engages around the edge of the inwardly facing lip and contracts the rear edge. When the position of hook 36 relative to base plate 4 and cover 20 is moved, typically in a forward direction, hook tip 38 engages the lip and forces the arch member in a forward direction which in turn forces the lower jaw in a forward direction to increase the opening of the breathing passages thus ameliorating the effects of snoring or sleep disorders.

One particularly preferred form of the complementary connecting means is one form of base plate 4 being the planar form without the flange located at the front and with the side wings 16 being also located in the common plane with body 6 of base plate 4. In this embodiment, hook top 38 engages with the inboard edge of base plate 4 to connect the two arches together to form the dental splint. This form of the complementary connector means allows the splint to adopt a low profile configuration which is more comfortable and compliant for the person wearing the splint.

Alternatively, the complementary connecting means 37 is a receiving means in the form of a groove, slot or similar for receiving the tip 38 of hook 36.

A particularly preferred form of the complementary engaging means 37 is planar plate. In this embodiment instead of all of the components of fastener 2 being used to form the arch member, only base plate 4 is used. This arch member does not have a fastener but only base plate 4.

In this embodiment the edge of base plate 4 is contacted by hook 36 associated with the fastener of the other arch member so that when the position of hook 36 is adjusted, typically in a forward direction, hook tip 38 engages against the edge of the plate to force the arch member having base plate 4 alone, typically in a forward direction.

It is to be noted that other embodiments of the dental splint having the fastener of the present invention are possible.

Manufacture of one of these other forms of the dental splint will now be described, particularly a mandibular dental splint incorporating the fastener 2 of the present invention enabling a low profile dental splint to be made will now be described.

A dentist, dental technician or other authorised health worker firstly takes an impression of a patient's teeth, including both the upper set of teeth and the lower set of teeth and uses the impressions to make a replica set of upper and lower teeth from a solid material such as for example, from ceramic, silicon or other suitable solid material or the like. The upper and lower set of replica teeth are then placed in an articulator allowing the upper set and lower set to move with respect to each other in a manner replicating or simulating movement of the jaw.

A quantity of a suitable thermoplastic material such as for example, a polymeric material or similar, such as erklloc pro is taken and formed into a planar blank. The blank of erklloc pro and the replica of the sets of teeth are placed in a suitable vacuum forming machine or pressure machine to produce casts or wings of the teeth. The casts or wings are made from the erklloc pro which is a double laminate functional splinting material that is a combination of harder and softer material in which the softer material is arranged against the teeth of the replica set of teeth. The casts are trimmed, shortened and reshaped to conform exactly to the impressions or replicas of the patient's teeth.

The final form of the casts after trimming and adjusting are once again placed on the impressions or replicas of the patient's teeth and are once again placed in the articulator.

When in the articulator, a viscous mix of acrylic material such as for example, erklloc pro or a similar material is prepared. The planar plate used as the complementary connecting means of one of the arches is placed on the cast and sufficient acrylic added to affix the plate to the cast. The cast is allowed to set rigid to securely affix the plate to the cast. If required, additional quantities of acrylic can be applied over the plate to further secure the plate to the cast so as to prevent it from becoming loose. Thus, the first arch member of the mandibular splint having the plate is formed.

The other arch member of the splint is now formed. A further quantity of acrylic material is added to the two tabs extending outwardly from the sides of the fastener and the fastener is located upon the plate so that the hook engages the lip. This allows the hook and lip to be aligned correctly with each other and for both to be located centrally within the splint. The articulator is closed so that the upper cast comes into contact with the base plate of the fastener to allow the acrylic around the tabs to adhere the base plate to the upper cast. As there is a gap or space between the upper cast and the lower cast, additional acrylic, if required, can be added to the base plate and evenly distributed to securely attach the fastener to the cast. It is to be noted that the base plate is embedded within, adhered to or otherwise bound to the second arch member.

The splint is then removed from the articulator and further trimmed if required and polished to form the splint.

The splint can then be fitted to the patient by the dentist or health worker and a final fitting adjustment can be made to determine the precise location of the hook so that the lower arch is moved forwardly to open the breathing passage during use of the splint.

If adjustment of the device is required, the patient can return to the dentist for further adjustment.

The approximate position of the hook 36 within slot 30 is determined by observation of the particular person's mouth and in accordance with markings 27. In this approximate position, in use of the dental splint of the present invention, the upper arch 50 containing the fastener is located within the mouth.

A second arch member, typically the lower arch member 48, having the complementary connecting or receiving means, say a lip or base plate 4 not having a flange is placed in the mouth against the lower teeth in an orientation opposite to that of upper arch 50.

When both upper and lower arch members 50,48 of the mandibular splint are placed separately in the mouth with the hook 36 of the upper arch in contact with the lip or the flange of the lower arch, the orientation of fastener 2 is such that aperture 26 is forwardly facing towards the mouth and thus provides easy access to the head of allen bolt 44. A suitable tool, such as an alien key or the like, is inserted into the mouth through aperture 26 to contact the head of allen bolt 44. The tool is rotated to rotate allen bolt 44 which in turn moves the position of hook 36 lengthwise along slot 30. Since hook 36 is in contact with the edge of plate of the lower arch 48, the lower arch is forced forward also. As the lower arch is moulded to lower teeth movement of the lower arch 48 forces the lower jaw forward so that the breathing passages are realigned or opened so that the breathing passage is less restricted thereby preventing snoring and improving breathing during sleep. A note of the position of hook 36 with respect to the graduations 27 is noted. Further adjustment of the device can be done by the person whilst the device is being worn by the person being treated. The splint can be readily adjusted by the wearer whilst it is located within the mouth, thereby obviating the need for a specialist technician or similar to adjust it. Further, as the treatment progresses further adjustment can be made in situ in accordance with new requirements to improve the success of the treatment.

Advantages of the present invention include the following:

The fastener of the present invention allows a more comfortable mandibular splint to be formed since there is no flange to cause annoyance or discomfort. Furthermore, the fastener and/or dental splint can adopt a low profile since the fastener is reduced in size by not having a flange, or the ends of the prongs extending outwardly.

The fastener can be supplied as a single low cost integral unit for attaching to an arch member to form the splint. Thus, the one fastener can be used with a variety of different arches.

Owing to the removal of the flange, the actual weight of the fastener, and hence the dental splint is reduced so that the splint is more comfortable to use and more compliant to wear. As well, the fasteners are less expensive to air freight owing to their reduced weight. The splint can be made at a lower cost because only the arch members need to be molded to the exact shape of a particular mouth and once made the fastener can be adhered to the arch.

The fastener can be adjusted at will in situ by the person using the splint as the need arises during use and during the treatment. Thereby obviating the need to make a multitude of splints of slightly different configurations during treatment of the patient.

The described arrangement has been advanced by explanation and many modifications may be made without departing from the spirit and scope of the invention which includes every novel feature and novel combination of features herein disclosed.

Those skilled in the art will appreciate that the invention described herein is susceptible to variations and modifications other than those specifically described. It is understood that the invention includes all such variations and modifications which fall within the spirit and scope.

The invention claimed is:

1. A fastener having a substantially planar arch-engaging profile suitable for connecting a plurality of arch members of a dental splint together in a predetermined spatial relationship when located within the mouth of a person for treating the person suffering from a sleep disorder, wherein the substantially planar arch-engaging profile allows the fastener to fit comfortably within the mouth of the person, the fastener comprising:

a substantially planar base member having a plurality of substantially planar attachment elements extending therefrom and in a common plane therewith to allow the fastener to define the substantially planar arch-engaging profile, a cover member adhered to the substantially planar base member to form a cavity therebetween, at least a part of a movable connector located within the cavity, and an adjustor at least a part of which is located within the cavity, said adjustor cooperative with the connector such that movement of the adjustor produces movement in the connector that in turn moves one of the plurality of arch members with respect to another of the plurality of arch members so as to adjust the splint to treat the person.

2. A fastener according to claim 1, in which a locator is provided in one wall of the cover for assisting in locating the adjustor within the cavity formed between the base member and the cover member.

3. A fastener according to claim 2 in which the wall of the cover member having the locator is the wall located at the front of the mouth when the dental splint is located within the mouth of the person.

4. A fastener according to claim 3 in which the locator is an aperture located in the front wall of the cover.

5. A fastener according to claim 1 in which the connector comprises a hook.

6. A fastener according to claim 5 in which the hook is provided with a shank and the shank is provided with an internally threaded aperture for receiving an externally threaded shaft so that rotation of the shaft within the aperture moves the hook with respect to at least one of the base plate and cover.

7. A fastener according to claim 6 in which the hook is provided with a curved portion located at or towards the tip of the hook.

8. A fastener according to claim 7 in which the cover is provided with a slot through which a part of the shank of the hook, is received for movement in a lengthwise extending direction of the slot.

9. A fastener according to claim 8 in which the side of the cover having the slot through which the shank of the hook extends is provided with graduations, markings or indicators forming a guide showing the extent of movement of the hook lengthwise along the lengthwise extending axis of the slot to assist in adjusting at least one of the fastener and dental splint.

10. A fastener according to claim 9 in which the graduations are in the form of a graduated scale comprising a multitude of regularly spaced apart substantially parallel lines formed on the face of the cover.

11. A fastener according to claim 6 in which the adjustor is a bolt having a head and an externally threaded shank arranged so that the head is located within or through the aperture forming the locator.

12. A fastener according to claim 11 in which the head of the adjustor is provided with a flange, skirt, or other enlarged portion to assist in retaining the adjustor within the cavity.

13. A fastener according to claim 12 in which the size of the aperture located in the front wall of the cover is less than the size of the enlarged portion of the head of the adjustor so as to assist in retaining the adjustor within the cavity.

14. A fastener according to claim 1 in which each of the attachment elements is a flap, tab or tag.

15. A fastener according to claim 14 in which the attachment elements are each provided with an aperture or a projection to assist in attaching the fastener to one of the arches in which the arch is made from polymeric plastics material.

16. A fastener according to claim 14 in which the fastener is attached to the base member by embedding the attachment elements in the polymeric plastics material of one of plurality of arch members or adhering or bonding the fastener to the one of the plurality of arch members.

17. A fastener according to claim 1 in which the connector engages a complementary connector in the other arch member that is in the form of a lip, shelf, groove, slot, flange, ring, loop or plate.

18. A fastener according to claim 17 in which the complementary connector is a planar plate or planar base plate arranged so that the connector engages the edge of the plate or base plate to move one of the plurality of arch members with respect to the other arch member so that at least one of the fastener and arch member can adopt the substantially planar arch-engaging profile when in the mouth of the person.

19. A fastener according to claim 18 in which the connector engages with a part of the complementary connector so that movement of the connector causes corresponding movement of the arch having the complementary connector to bring the arch having the complementary member forward with respect to the arch having the fastener thereby altering the shape of the airway of the person using the fastener to reduce or prevent snoring.

20. A fastener according to claim 1 in which the cover member and base member are adhered to each other by welding to more securely attach the cover and base plate to each other to prevent the fastener from becoming loose in use.

21. A fastener according to claim 1 in which one of the plurality of arch members is an upper arch and the other of the plurality of arch members is a lower arch in which the fastener is attached to the upper arch.

22. A mandibular splint for treating a person suffering from a sleep disorder, said splint including two arch members connectable together in use of the splint, wherein at least one of the arch members includes a fastener for connecting the two arch members in a prearranged or predetermined spatial relationship when located within the mouth of a person for treating the person suffering from a sleep disorder, to ameliorate the effect of the sleep disorder, said fastener defining a substantially planar arch-engaging profile allowing the fastener to fit comfortably within the mouth of the person, said fastener comprising a substantially planar base member having a plurality of substantially planar attachment elements extending therefrom and in a common plane therewith to allow the fastener to define the substantially planar arch-engaging profile;

a cover member adhered to the substantially planar base member to form a cavity therebetween;

at least a part of a movable connector located within the cavity and configured to move the arch member relative to the other arch member; and an adjustor at least a part of which is located within the cavity, the adjustor cooperative with the connector such that movement of the adjustor changes the position of one of the arch members with respect to the other through the connector in order to adjust the splint to treat the person.

23. A mandibular splint according to claim 22 in which the two attachment elements are embedded in the plastics material of the arch to which the fastener is attached.

24. A method of treating a person suffering from a sleep disorder with a dental splint according to claim 22 in which the attachment elements of the fasteners are embedded in the plastics material of the arch member.

25. A method of forming an arch member of a dental splint for use in treating a person suffering from a sleep disorder comprising:

forming a replica of at least some of the teeth of a person, forming a cast or mould from the replica of the teeth from a polymeric material attaching a fastener in the cast or mould or adhering the fastener to the cast or mould, wherein the fastener is suitable for connecting two parts of a dental splint together in a prearranged or predetermined spatial relationship in use when treating a person suffering from a sleep disorder, wherein the fastener has a substantially planar arch-engaging profile allowing the fastener to fit comfortably within the mouth of the person, said fastener comprising a substantially planar base member having a plurality of substantially planar attachment elements extending therefrom and in a common plane therewith to allow the fastener to define the substantially planar arch-engaging profile;

a cover member adhered to the substantially planar base member to form a cavity therebetween;

at least a part of a movable connector located within the cavity and configured to move the arch member relative to the other arch member; and an adjustor at least a part of which is located within the cavity, the adjustor cooperative with the connector such that movement of the adjustor changes the position of one of the arch members with respect to the other through the connector in order to adjust the splint to treat the person.

26. A method of forming an arch member of a dental splint for use in treating a person suffering from a sleep disorder according to claim 25 in which the attachment elements are embedded in the plastics material of the arch member.

27. An arch member of a mandibular splint for use in treating a person suffering from a sleep disorder, the arch member including a fastener wherein the fastener has a substantially planar arch-engaging profile suitable for connecting the arch member to another arch member forming the mandibular splint together in a prearranged or predetermined spatial relationship when located within the mouth of a person for treating the person suffering from a sleep disorder, to ameliorate the effect of the sleep disorder, wherein the fastener comprises:

a substantially planar base member having a plurality of substantially planar attachment elements extending therefrom and in a common plane therewith to allow the fastener to define the substantially planar arch-engaging profile;

a cover member adhered to the substantially planar base member to form a cavity therebetween;

at least a part of a movable connector located within the cavity and configured to move the arch member relative to the other arch member; and an adjustor at least a part of which is located within the cavity, the adjustor cooperative with the connector such that movement of the adjustor changes the position of one of the arch members with respect to the other through the connector in order to adjust the splint to treat the person.

28. A method of treating a person suffering from a sleep disorder with a dental splint wherein the dental splint comprises:

a first and a second arch members wherein the first arch member is provided with an adjustable fastener for connection to the second arch member to interconnect the two arch members together;

said method including the steps of either sequentially or simultaneously locating the two arch members either in combination or separately in the oral cavity of the person, connecting the two arch members together if required, and selectively adjusting the position of the two arch members with respect to each other by adjusting the adjustable fastener wherein, the adjustable fastener provided attached to the first arch member has a substantially planar arch-engaging profile suitable for connecting the first and second arch members together in a prearranged or predetermined spatial relationship when located within the mouth of a person for treating the person suffering from a sleep disorder, to ameliorate the effect of the sleep disorder, said substantially planar arch-engaging profile allowing the fastener to fit comfortably within the mouth of the person, said fastener comprising a substantially planar base member having a plurality of substantially planar attachment elements extending therefrom and in a common plane therewith to allow the fastener to define the substantially planar arch-engaging profile;

a cover member adhered to the substantially planar base member to form a cavity therebetween;

at least a part of a movable connector located within the cavity and configured to move the arch member relative to the other arch member; and an adjustor at least a part of which is located within the cavity, the adjustor cooperative with the connector such that movement of the adjustor changes the position of one of the arch members with respect to the other through the connector in order to adjust the splint to treat the person.

* * * * *